United States Patent [19]
Kelley

[11] Patent Number: 5,334,172
[45] Date of Patent: Aug. 2, 1994

[54] FLUID APPLICATOR FOR OCULAR PROSTHESIS

[76] Inventor: Kevin V. Kelley, 63 Bradford Way, Voorhees, N.J. 08043

[21] Appl. No.: 990,053

[22] Filed: Dec. 14, 1992

Related U.S. Application Data

[63] Continuation-in-part of Ser. No. 892,980, Jun. 3, 1992, Pat. No. 5,171,265.

[51] Int. Cl.$^5$ .................... A61F 2/14; A61M 35/00
[52] U.S. Cl. ........................... 604/300; 623/4
[58] Field of Search .............. 604/294–302; 623/4

[56] References Cited

U.S. PATENT DOCUMENTS
3,364,501  1/1968  Stafford .
4,629,456 12/1986  Edwards ..................... 604/294

FOREIGN PATENT DOCUMENTS
2203048 10/1988 United Kingdom .

OTHER PUBLICATIONS

Artificial Eyes & Tear Measurements–Allen et al–American Academy of Ophthalmology pp. 155–157.
The Anopthalmic Socket the Prosthetic Eye–Vasquez et al Ophthalmic Reconstructive Surgery pp. 277–280.
A Dictionary of Terms for the Ocularist–Kelley et al Jun. 1, 1974 pp. 10, 11, 12 & 16.
BioCoat TM Opt-BioCoat Products The Making of a Hollow Prosthetic Eye.

Primary Examiner—Randall L. Green
Assistant Examiner—Mary Beth Jones
Attorney, Agent, or Firm—Thomas A. Lennox

[57] ABSTRACT

A device and method for injecting fluids into a self-lubricating ocular prosthesis with an orifice to a bore opening into a chamber to hold the fluid, the device including a compressible container to hold the fluid, with a hollow tubular nozzle with a pointed end tip that seats it into the orifice such that a seal is accomplished to allow squirting the fluid into the one-half millimeter orifice.

23 Claims, 3 Drawing Sheets

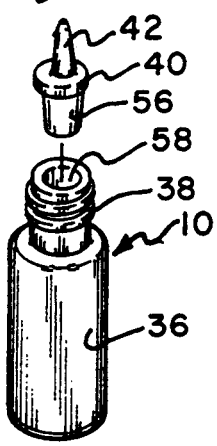
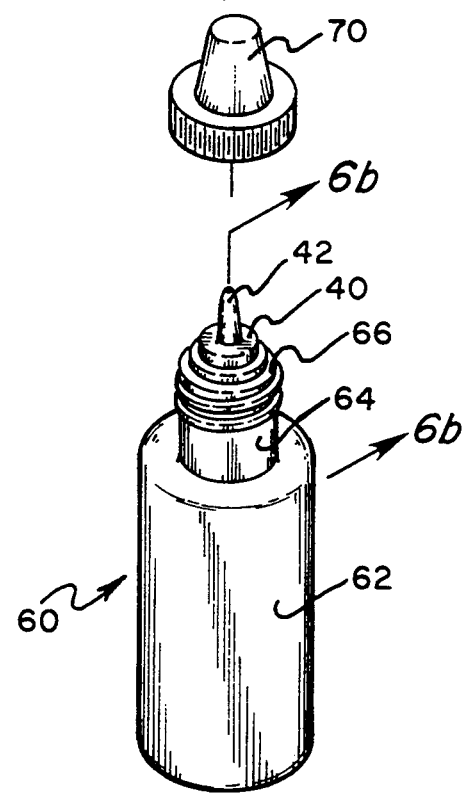
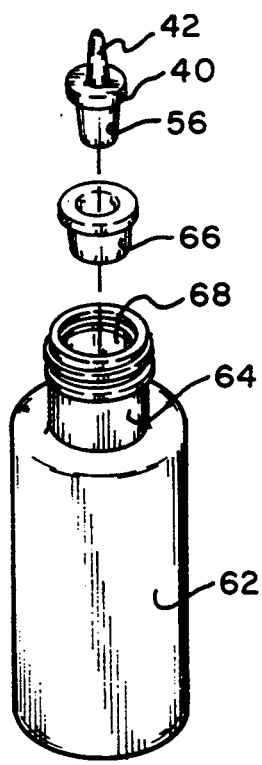
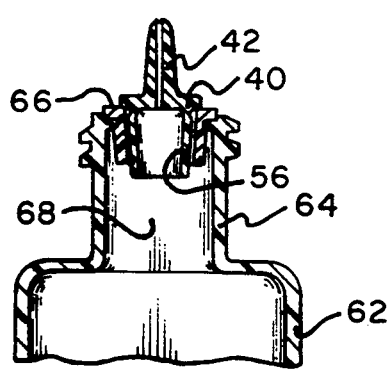
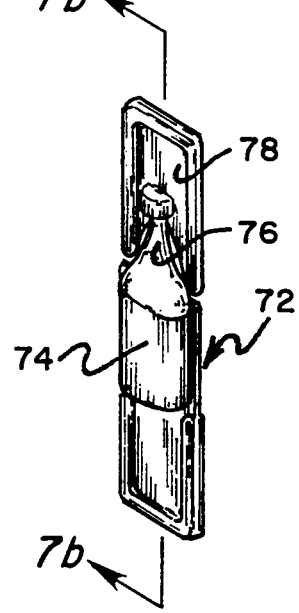

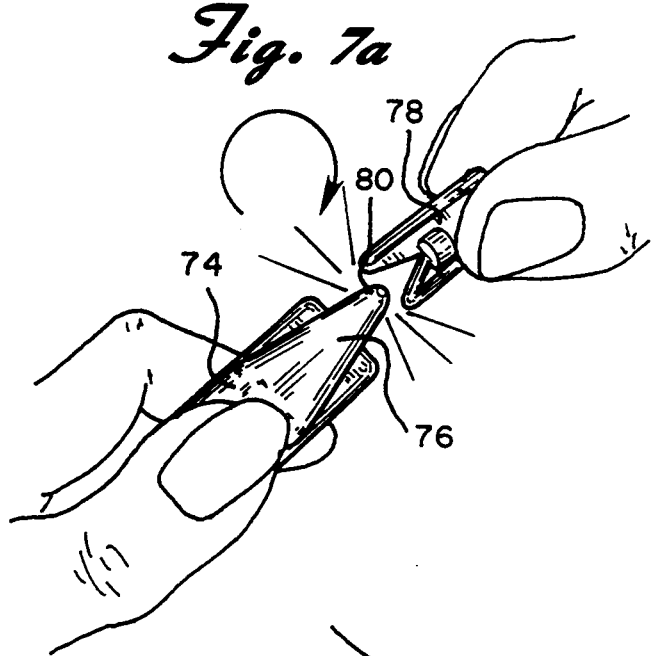
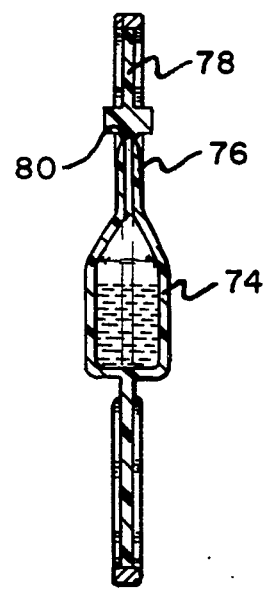
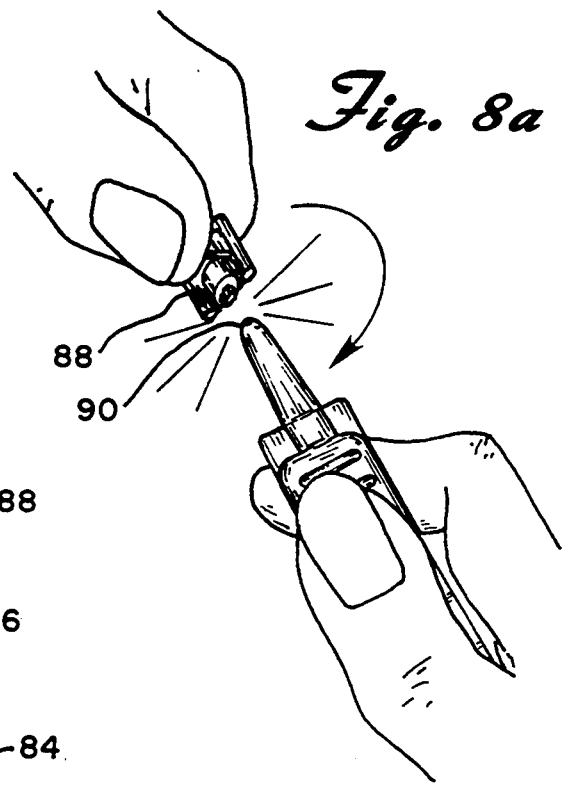
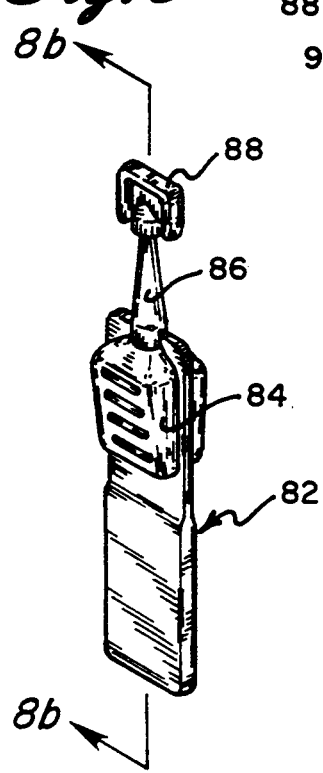
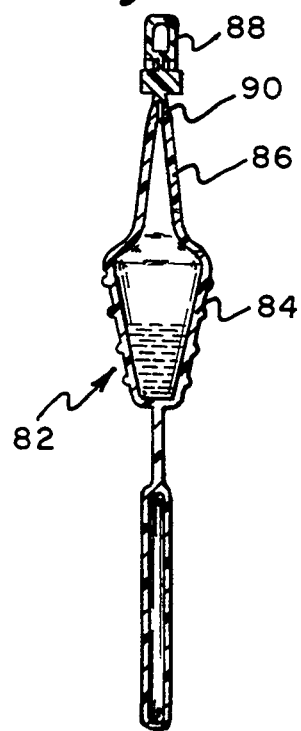

FLUID APPLICATOR FOR OCULAR PROSTHESIS

This application is a continuation in part of co-pending application Ser. No. 07/892,980 filed Jun. 3, 1992 now issued as U.S. Pat. No. 5,171,265 and is of common inventorship.

BACKGROUND OF THE INVENTION

This invention involves a fluid applicator for an ocular prosthesis and more particularly a device to inject fluids into a cavity of a self-lubricating ocular prosthesis.

In the co-pending application, now U.S. Pat. No. 5,171,265 there is shown in FIG. 8 and described in the specification a device and method of injecting fluids into a cavity of the ocular prosthesis through bore opening 36 through anterior surface 28 of the prosthesis. That United States Patent is incorporated herein by reference thereto. The use of applicator device 90 in said patent or applicator 114 illustrated in FIG. 12 of U.S. Pat. No. 3,364,501 to W. F. Stafford, poses certain problems. Firstly, since the bore opening through the anterior surface is commonly about one-half millimeter, the diameter of tube nozzle 92 of device 90 in said co-pending application must be of a smaller diameter. The tube must have sufficient wall thickness for structural integrity so that the lengthwise tubular bore can only be a few mils in diameter. This makes the injection of viscous or even thixotropic fluids difficult or even impossible. Throughout the specification and claims, the term "fluid" is intended to include all materials that can be caused to flow under pressure at room or slightly elevated temperatures. The "fluid" materials include highly viscous materials such as petroleum jelly and highly viscous emulsions. Further, it is difficult to choose a length for tube 92, which is long enough to handle and reach into the interior cavity of the prothesis and not be so long that it engages the cap releasably closing the access passage through the posterior surface of the body of the prosthetic eye. If the tube engages that cap, it may partially or fully dislodge the cap of the prosthesis. In addition, great care must be taken to remove tube 92 before any pressure is released on the bottle of applicator 90 or fluid will be drawn back into the applicator device. This not only contaminates the material in the device, but provides an incomplete fill of the chamber.

All prior art devices and methods fail to satisfy the needs and the problems described above and attain the objects of the present invention described hereinbelow.

SUMMARY OF THE INVENTION

It is a particular object of the present of the invention to provide an applicator device which the patient can easily use to inject fluids into an ocular prosthesis while it is still present in the eye socket. As noted in the co-pending application, now U.S. Pat. No. 5,171,265, it is a great advantage of my new prosthesis, that it can remain in the eye socket for extended periods of time to avoid all the risks and disadvantages described in the parent application. It is therefore most desirable that the patient be able to fill the chamber or chambers of my ocular prosthesis on a regular basis over a period of weeks.

A particular object of the present invention is to provide an applicator and method by which the patient can locate a bore opening through the anterior surface of the body by touching the tip of the new device to the anterior surface and move it around until it engages the bore opening. It has been found that it is best to round off the edges of the bore opening on the anterior surface to reduce the possibility of irritation of a covering eyelid and it is further preferred that a slight concave depression a few mils deep be provided surrounding the peripheral edge of the orifice of the bore opening. With this depression the patient can easily move the tip of the applicator across the anterior surface in a circular motion until the tip "drops into" engagement with the orifice and seats in of the bore opening.

It a further object of the present invention to provide an easier method to add fluids to the chamber of the self-lubricating ocular prosthesis when it has been removed from the eye. When the prosthesis has been removed from the eye, it is certainly satisfactory to open the cap over the access passage through the posterior surface of the body. That process can be tricky as it is necessary to fill the chamber, and reseat the cap, all without adulterating the prosthesis or the materials being placed in the cavity. Further, while adding liquid to the chamber from the posterior opening, the more fluid liquids leak out the bore opening in the anterior surface. It is well known that handling the prosthesis increases the chance that harmful bacteria may ultimately reach the eye socket and may provide an irritation or possible damage. With the present invention, less handling is required, particularly that of the posterior surface of the prosthetic eye body.

It is an additional object of the present invention to provide a device and method that substantially reduces or eliminates the possibility of drawing fluid back into the bottle applicator. When the present invention is used, any significant tilting of the applicator, will break the seal with the orifice, breaking the vacuum and avoiding any fluid being sucked back into the applicator device.

It is an object of the present invention to provide an applicator with a tip that is safer to use in the event of an unintended use by the patient or any third parties in a natural eye. While an application of fluid to a natural eye is not recommended with any pointed tip, it must be recognized that patients, and third persons, particularly children, might attempt to use the applicator device in a natural eye, against the recommendations of the supplier of the applicator. The tip of the present invention is much more blunt then a small diameter tube which could more easily injure a natural eye. Further, a tip of the present invention can be used to push the lid aside to contact the bore opening while being less likely to irritate the lid of the wearer of the ocular prosthesis.

It is a particular object of the present invention to provide an applicator device that can be used by one hand, since the slightly rounded tip of the present invention can be used to push aside the eyelid out of the way and expose the bore opening into the prosthesis.

It is an object of the present invention to provide an applicator device that can allow the reduction of the size of the bore opening through the anterior surface of the prosthesis to a smaller diameter and still allow the injection of fluids into the cavity while providing a satisfactory exit opening for fluids from the cavity to the lid and the eye socket.

It is a specific object of the present invention to provide a tip that may be attached to virtually any size and shape flexible container.

A particular object of the present invention is to provide an end tip shape on the applicator that will "seat" into the aperture of the bore opening in the anterior surface of the prosthesis. For example, a typical applicator tip for natural eyes is on the classic "toothpaste" type tube used for the application HYPO-TEARS ® ointment supplied by the Johnson and Johnson Company Iolab Pharmaceuticals, Division of Iolab Corporation, Claremont, Calif. 91711, that applicator tube tip is of relatively small diameter, but is not sufficiently pointed at the end such that it will not effectively seat in a half mil orifice through a convex surface, even when there is a slight depression provided. A preferred object of the present invention is to provide a tip end that will seat in the aperture, and engage only the peripheral edge of the anterior surface around the orifice.

It should be understood that the term "peripheral edge" includes a surface caused by rounding off that edge or even forming a truncated surface, essentially cutting off the corner of that peripheral edge. It is preferred that a side angled surface of the pointed tip of the present invention engage the peripheral edge on as wide a circular surface strip of the peripheral edge as possible, however the operation of the invention is satisfactory if only a line edge of that peripheral edge engages the side surface of the pointed tip of the applicator device. From a practical standpoint, that peripheral edge around the bore opening is normally rounded slightly to avoid any sharp edges, thereby providing a somewhat broader band of contact between the tip and that peripheral edge. It is most preferred that the outside surface of the pointed end tip of the applicator device of the present invention be a complimentary match of the angle of the peripheral edge around the bore opening of the ocular prosthesis.

It is an object of the present invention to provide a device containing or being capable of containing a fluid with means to apply pressure to that fluid to cause the fluid to flow out through a nozzle and ultimately out through a pointed tip of that nozzle. The container body may be of any suitable shape and construction and certainly includes the standard liquid bottle applicators, the toothpaste tube shape, and all of the single use dosage tip applicator shapes all of which depend upon finger pressure on the outside of the container body to supply the pressure. Other more complicated devices to apply the pressure are also suitable.

An aspect of the invention is a method for injecting fluids into a self-lubricating ocular prosthesis for use in a person's orbital cavity. The prosthesis includes a solid rigid prosthetic eye body that includes an anterior convex surface through which an iris-cornea-sclera simulation is visible and a posterior surface, proximately conforming to a surface of the person's orbital cavity. The prosthesis further incudes at least one chamber in the body defining a reservoir volume, an access passage from the first chamber through the posterior surface of the body, and a cap releasably closing the access passage. The prosthesis also includes a bore opening from the chamber through an orifice in the anterior surface of the body, there being a peripheral edge of the anterior surface around the orifice. The method includes providing an applicator device that includes a container that includes an open topped cavity adapted to be filled with a fluid to be injected into the chamber of the prosthesis. The applicator device further includes a hollow tubular nozzle that includes a lengthwise tubular bore operatively connectable at an inside end to the open topped cavity of the container and having an outside end opening, a pointed outside end tip surface surrounding the outside end opening, and seating means that when the end tip surface is engaged against the orifice in the anterior surface of the eye body, the end tip surface seats and seals said surface in the orifice. The applicator device further includes ejection means to cause pressure on the fluid to flow out of the container into the tubular bore of the nozzle and out the outside end opening through the end tip. The method further includes filling the cavity of the container with a fluid. The method also includes locating the orifice by touching and moving the end tip of the nozzle on the anterior surface of the prosthesis. The method then includes seating the end tip surface in the orifice, pressuring the end tip of the nozzle to the orifice, and, while maintaining that pressure, operating the ejection means to eject fluid from the cavity of the container through the tubular bore of the nozzle into the bore opening through the anterior surface of the prosthesis and into the chamber.

It is preferred that the self-lubricating ocular prosthesis be in the person's orbital cavity and the locating the orifice includes touching and moving the end tip of the nozzle on the anterior surface of the prosthesis while the prosthesis is in the eye socket. It is further preferred that the self-lubricating ocular prosthesis further include a depression in the anterior convex surface around the orifice and the locating the orifice includes touching and moving the end tip of the nozzle on the depression on the anterior surface of the prosthesis. It is further preferred that the seating means prevents the nozzle from significantly entering into the orifice bore opening through the anterior surface of the prosthesis when seating the end surface of the end of the nozzle. It is further preferred that the seating means include a diameter of the end surface larger than the bore opening and smaller than a depression in the anterior surface of the eye body around the orifice. It is further preferred that the seating includes engaging the tip end surface only against the peripheral edge of the anterior surface around the orifice.

A second aspect of the invention is a method for injecting fluids into a self-lubricating ocular prosthesis for use in a person's orbital cavity including firstly providing a prosthesis as described above. The method then includes providing an applicator device as described above. The method then includes filling the cavity of the container with a fluid and locating the orifice by touching and moving the end tip of the nozzle on the anterior surface of the prosthesis. The method further includes seating the end tip surface in the orifice, pressuring the end tip of the nozzle to the orifice, and, while maintaining that pressure operating the ejection means to eject fluid from the cavity of the container through the tubular bore of the nozzle into the bore opening through the anterior surface of the prosthesis and into the chamber.

A third aspect of the invention is a method for injecting fluids into a self-lubricating ocular prosthesis for use in a person's orbital cavity, the prosthesis being as described above. The method includes providing an applicator device that includes a container that in turn includes an open topped cavity containing a fluid to be injected into the chamber of the prosthesis. The device further includes a hollow tubular nozzle, ejection means, and connection means, all as described above. The device further includes closure means to releasably close the end opening of the nozzle. The method further includes releasing the closure means and locating the orifice by touching and moving the end tip of the nozzle on the anterior surface of the prosthesis. The method further includes seating the end tip surface in the orifice, pressuring the end tip of the nozzle to the orifice, and, while maintaining that pressure, operating the ejection means to eject fluid from the cavity of the container through the tubular bore of the nozzle into the bore opening through the anterior surface of the prosthesis and into the chamber.

A fourth aspect of the invention is a device for injecting fluids into a self-lubricating ocular prosthesis while in a person's orbital cavity, the prosthesis being as described above. The device includes a container including an open topped cavity filled with a fluid to be injected into a chamber of the prosthesis and a hollow tubular nozzle as described above. The device further includes ejection means to cause pressure on the fluid to flow out of the container into the tubular bore of the nozzle and out the outside end opening through the end tip, connection means to connect the nozzle in the open top of the cavity, and closure means to releasably close the end opening of the nozzle.

It is preferred that the end tip of the nozzle be composed of a polyolefin polymeric plastic. It is also preferred that the ejection means include a compressible container.

A fifth aspect of the invention is device for injecting fluids into a self-lubricating ocular prosthesis while in a person's orbital cavity, the prosthesis being as described above. The device includes a container that includes an open topped cavity adapted to be filled with a fluid to be injected into a chamber of the prosthesis and a hollow tubular nozzle as described above. The device further includes ejection means to cause pressure on the fluid to flow out of the container into the tubular bore of the nozzle and out the outside end opening through the end tip, and connection means to connect the nozzle in the open top of the cavity.

BRIEF DESCRIPTION OF THE DRAWINGS

FIG. 5a is an exploded view thereof.

FIG. 5b is a partial cross-sectional view taken along lines 5b—5b of FIG. 5.

FIG. 6 is a perspective view of a second embodiment of a device of the present invention.

FIG. 6a is a exploded view thereof.

FIG. 6b is cross-sectional view taken along lines 6b—6b of FIG. 6.

FIG. 7 is a perspective view of a third embodiment of the present invention.

FIG. 7a is a perspective view showing the opening process thereof.

FIG. 7b is a cross-sectional view taken along lines 7b—7b of FIG. 7.

FIG. 8 is a perspective view of a fourth embodiment of the present invention.

FIG. 8a is a perspective view showing the opening process thereof.

FIG. 8b is a cross-sectional view taken along lines 8b—8b of FIG. 8.

DESCRIPTION OF PREFERRED EMBODIMENTS

Figure 1:
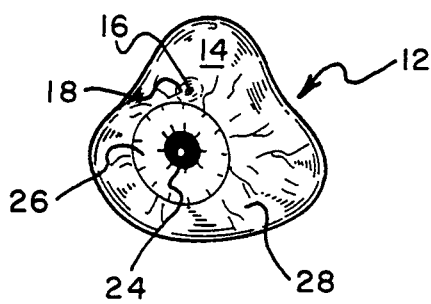
FIG. 1 is a frontal perspective view showing the anterior surface of an ocular prosthesis.
Figure 2:
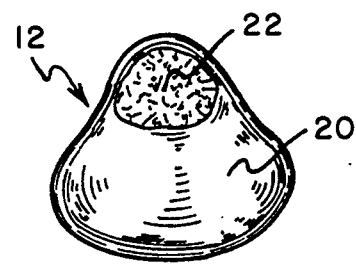
FIG. 2 is a rear perspective view thereof showing the posterior surface of the prosthesis.
Figure 3:
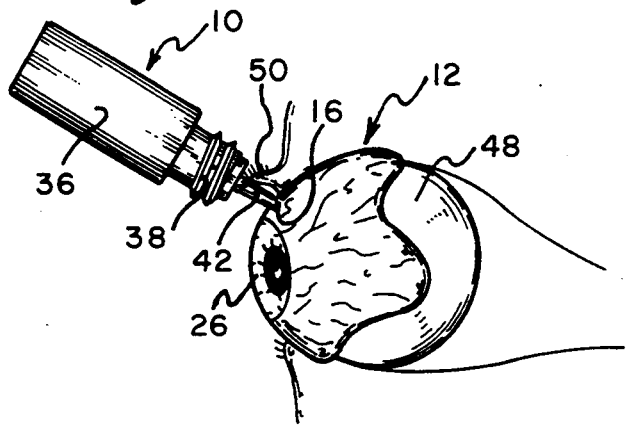
FIG. 3 is a perspective view showing a device and method of the present invention injecting fluid into the prosthesis.
Figure 4A:
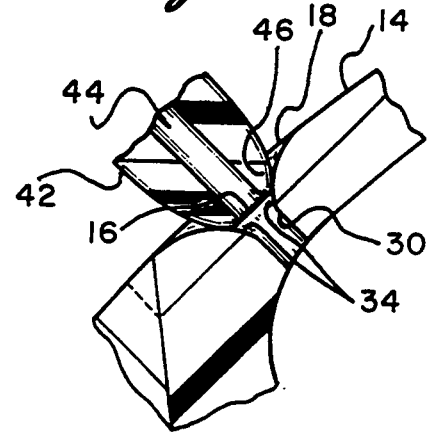
FIG. 4a is an enlarged view of a portion of FIG. 4.
Figure 4:
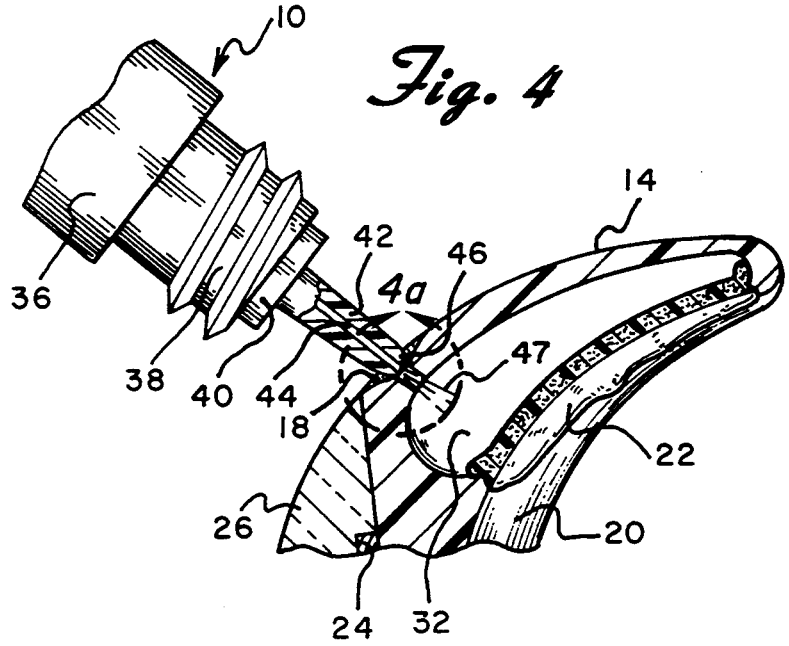
FIG. 4 is an enlarged view with a partional cross section showing engagement of the device and filling the cavity of the prosthesis with fluid.
Figure 5:
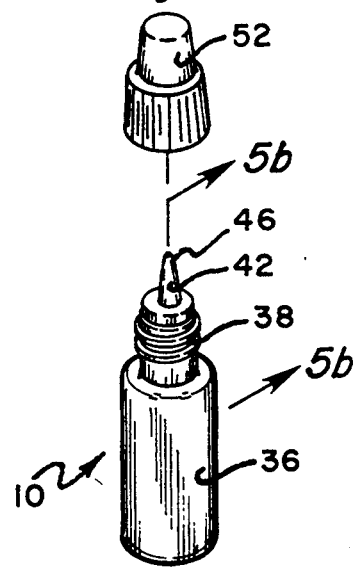
FIG. 5 is a perspective view of the applicator device illustrated in FIG. 3.

In FIGS. 1, 2 and 3 ocular prosthesis 12 is illustrated in various views as conformed and produced by copending application Ser. No. 07/892,980, incorporated herein by reference thereto. Prosthesis 12 includes anterior surface 14 through which orifice 16 of a bore to interior chamber 32 as more fully illustrated in the enlarged partially cross-sectional view of FIG. 4. A depressed area 18 surrounds orifice 16 produced by a slight leveling and rounding off of the peripheral edges of the orifice. In FIG. 2 posterior surface 20 is shown through which cap 22 opens to chamber 32. The simulations of iris 24, cornea 26 and sclera 28 are viewed through anterior surface 14 of the prosthesis. As shown in FIG. 4, applicator device 10 with fluid container 36 is injecting fluid 47 into chamber 32. In the enlarged view in FIG. 4a peripheral edge 34 of orifice 16 opening into bore opening 30 is displaced. Device 10 included threaded neck 38 capable of receiving cap 52 to close and protect tubular nozzle 42 which is an integral part of barrel insert 40 which engages into neck 38 with a press snap fit. Nozzle 42 has lengthwise tubular bore 44 which opens into the supply of liquid in container body and through an opening in end tip 46, which is rounded and easily seats into orifice 16. In FIG. 3, device 10 is shown positioned close to perpendicular to the anterior surface 14 engaging orifice 16 under eyelid 50. The applicator is a polyethylene 3.0 CC cylindrical bottle round molded of low density polyethylene Catalog Number 20319-82 from Wheaton Plastics, Mill and Wymouth Road, Mays Landing, N.J. Tubular nozzle 42 is an integral molding with barrel unit 40, also molded out of low density polyethylene with a 0.014 millimeter tip with an eight millimeter diameter barrel unit insertable and forming a force fit into the opening of container 36. This tip unit is Catalog Number 12086-24, also from Wheaton Plastics. Cap 52 is catalog number 15055-01 also from Wheaton Plastics threadably engagable on neck 38. As is shown in FIG. 4, end tip surface 46 seats in orifice 16 effectively sealing the opening and allowing fluid 47 to be injected through tubular bore 44 into chamber 32. As illustrated in FIG. 4a, the shape of depressed area 18 provides an effective means of locating orifice 16 and allowing end tip 46 to seat. In FIG. 4a depressed area 18 is a shallow depth of only a few mils below convex surface 14. In order to avoid any possible irritation of eyelid 50, it is desirable to polish off the peripheral edge 34 of the orifice opening to bore 30 of about 0.5 millimeter diameter. With this method bores of one-quarter millimeter are quite satisfactory. This has the added advantage of allowing end tip 46 to easily seat and seal off the opening during the injection process. As shown in FIGS. 5a and 5b, barrel insert 40 includes lower cylindrical body 56 which force fits into top opening 58 of threaded neck 38 of device 10.

Device 60 is illustrated in FIG. 6 with an exploded view illustrated in FIG. 6a and an upper vertical cross-sectional view provided in FIG. 6b. Standard one-half ounce polyethylene container 62 is equipped with threaded neck 64 into which coupler unit 66 made from Wheaton Plastics Catalog Number 11953 of fifteen millimeter dropper tip with a 0.018 inch tip opening. Since this tip is too blunt for the smaller bore openings into the prosthesis, it is cut off leaving coupler insert 66 which snap fits into opening 68 of neck 64. The inside diameter of coupler unit 66 with the tip cut off receives base cylinder 56 of barrel insert 40 which seals tubular nozzle 42 to the top of device 60. Similarly, the small nozzle tip can be connected to a variety of bottle sizes and shapes.

A trend in packaging is illustrated in FIGS. 7 and 8 showing how the present invention can be incorporated in premolded sealed packaging units which are broken apart by the customer to generally dispense a single dose quantity. FIG. 7 is a modified version of a packaging unit containing CELLUVISC® lubricant ophthalmic solution from Allergam Pharmaceuticals a Division of Allergon Inc. Irvine, Calif. 9214-92713. The public used container has a tip designed to be used around natural eyes and is therefore blunt and ineffective in the present invention. The device in FIG. 7 includes a modified tip shape to be effective with the present invention. Device 72 includes container body 74 which necks down to tip 76, the open end of which is open by twisting flange member 78 as shown in FIG. 7a to expose end tip 80. Similarly, lubricant eye drops are supplied by CIBA Vision Ophthalmics of Atlanta, Ga. and supplied in a container similar to that illustrated in FIG. 8, 8a and 8b. Again the CIBA Vision product is intended to be used around the natural eye and is therefore very blunt to avoid damaging the eye. In device 82, container body 84 is connected to nozzle neck 86 molded closed by top member 88. As shown in FIG. 8a flange member 88 is twisted open and exposing end tip 90 shaped to seat in the bore opening of the prosthesis.

The standard toothpaste tube manufactured in metal is used in packaging the product HYPOTEARS® bedtime lubricating eye ointment by Johnson and Johnson Company, Iolab Pharmaceuticals, of Claremont, Calif. 91711. Again the end tip of the tube is rounded and blunt for safety purposes in natural eyes and is not effective in engaging the orifice of the prosthesis. The tip can be reshaped for use in the present invention.

The use of a polyolefin plastic of the tip of the present, softer than the prosthesis surface, avoids scratching the surface and allows the end tip to easily seat and effectively seal in the orifice. The shape of end tip 46 must be sufficiently pointed to engage and seat in the orifice of the bore opening through the anterior surface of the prosthesis which may have a diameter less than one-half millimeter down to about one-quarter millimeter. The effective diameter of the orifice is widened to some extent by the polishing operation which tends to form a slight funnel shape at the orifice opening at the orifice of the bore opening. The tubular bore of the tubular nozzle must be a smaller diameter then the orifice opening. The outside diameter of the tip at the end of the end tip has a diameter slightly smaller then the orifice to allow effective seating. The device must be held normal to the convex surface to obtain the best seal, although it is possible to slightly angle the applicator and still maintain a seal during the injection process, once the end tip is seated in the orifice. With the method, liquids as fluid as water as well as semi-solid thixotropic mixtures can be injected. Fluids as thick as petroleum jelly may be injected into the chamber of the prosthetic eye. The term "fluid" is intended to include all such materials that can be flowed under pressure at room or slightly elevated room or slightly elevated temperatures.

While this invention has been described with reference to the specific embodiments disclosed herein, it is not confined to the details set forth and the patent is intended to include modifications and changes which may come within and extend from the following claims.

I claim:

1. A method for injecting fluids into a self lubricating ocular prosthesis for use in a person's orbital cavity, the prosthesis comprising:
   (i) a solid rigid prosthetic eye body comprising an anterior convex surface through which an iris-cornea-sclera simulation is visible and a posterior surface, proximately conforming to a surface of the person's orbital cavity,
   (ii) at least one chamber in the body defining a reservoir volume,
   (iii) an access passage from the at least one chamber through the posterior surface of the body,
   (iv) a cap releasably closing the access passage, and
   (v) a bore opening from the at least one chamber through an orifice in the anterior surface of the body, there being a peripheral edge of the anterior surface around the orifice, the method comprising:
   (I) providing an applicator device comprising:
      (A) a container comprising an open topped cavity adapted to be filled with a fluid that can be injected into the chamber of the prosthesis, and
      (B) a hollow tubular nozzle comprising:
         (i) a lengthwise tubular bore operatively connectable at an inside end to the open topped cavity of the container and having an outside end opening,
         (ii) a pointed outside end tip surface surrounding the outside end opening, and
         (iii) seating means that when the end tip surface is engaged against the orifice in the anterior surface of the eye body, the end tip surface seats and seals in the orifice,
   (II) filling the cavity of the container with a fluid,
   (III) locating the orifice by touching and moving the end tip surface of the nozzle on the anterior surface of the prosthesis,
   (IV) seating the end tip surface in the orifice, pressuring the end tip surface of the nozzle to the orifice, and, while maintaining that pressure,
   (V) ejecting fluid from the cavity of the container through the tubular bore of the nozzle into the bore opening through the anterior surface of the prosthesis and into the chamber.

2. The method of claim 1 wherein the self lubricating ocular prosthesis is in the person's orbital cavity and the locating the orifice comprises touching and moving the end tip surface of the nozzle on the anterior surface of the prosthesis.

3. The method of claim 1 wherein the self lubricating ocular prosthesis further comprises a depression in the anterior convex surface around the orifice and the locating the orifice comprises touching and moving the end tip surface of the nozzle on the depression on the anterior surface of the prosthesis.

4. The method of claim 1 wherein the seating means prevents the nozzle from significantly entering into the orifice bore opening through the anterior surface of the prosthesis when seating the end tip surface of the nozzle.

5. The method of claim 1 wherein the seating means comprises a diameter of the end tip surface larger than the bore opening and smaller than a depression in the anterior surface of the eye body around the orifice.

6. The method of claim 1 wherein the seating comprises engaging only the end tip surface against the peripheral edge of the anterior surface around the orifice.

7. The method of claim 1 wherein the end tip surface of the nozzle is composed of a polyolefin polymeric plastic.

8. The method of claim 1 wherein the container is compressible.

9. A method for injecting fluid into a self lubricating ocular prosthesis for use in a person's orbital cavity comprising:
(A) providing a prosthesis comprising:
 (i) a solid rigid prosthetic eye body comprising an anterior convex surface through which an iris-cornea-sclera simulation is visible and a posterior surface, proximately conforming to a surface of the person's orbital cavity,
 (ii) at least one chamber in the body defining a reservoir volume,
 (iii) an access passage from the at least one chamber through the posterior surface of the body,
 (iv) a cap releasably closing the access passage, and
 (v) a bore opening from the chamber the at least one through an orifice in the anterior surface of the body, there being a peripheral edge of the anterior surface around the orifice,
(B) providing an applicator device comprising:
 (i) a container comprising an open topped cavity adapted to be filled with a fluid that can be injected into the chamber of the prosthesis,
 (ii) a hollow tubular nozzle comprising:
  (a) a lengthwise tubular bore operatively connectable at an inside end to the open topped cavity of the container and having an outside end opening,
  (b) a pointed outside end tip surface surrounding the outside end opening, and
  (c) seating means that when the end tip surface is engaged against the orifice in the anterior surface of the eye body, the end tip surface seats and seals in the orifice,
(C) filling the cavity of the container with a fluid,
(D) locating the orifice by touching and moving the end tip surface of the nozzle on the anterior surface of the prosthesis,
(E) seating the end tip surface in the orifice, pressuring the end tip surface of the nozzle to the orifice, and, while maintaining that pressure,
(F) ejecting fluid from the cavity of the container through the tubular bore of the nozzle into the bore opening through the anterior surface of the prosthesis and into the chamber.

10. The method of claim 9 wherein the self lubricating ocular prosthesis is in the person's orbital cavity and the locating the orifice comprises touching and moving the end tip surface of the nozzle on the anterior surface of the prosthesis.

11. The method of claim 9 wherein the self lubricating ocular prosthesis further comprises a depression in the anterior convex surface around the orifice and the locating the orifice comprises touching and moving the end tip surface of the nozzle on the depression on the anterior surface of the prosthesis.

12. the method of claim 9 wherein the seating means comprises a diameter of the end tip surface larger than the bore opening and smaller than a depression in the anterior surface of the eye body around the orifice.

13. The method of claim 9 wherein the seating comprises engaging only the end tip surface against the peripheral edge of the anterior surface around the orifice.

14. The method of claim 9 wherein the end tip surface of the nozzle is composed of a polyolefin polymeric plastic.

15. The method of claim 9 wherein the container is compressible.

16. A method for injecting fluids into a self lubricating ocular prosthesis for use in a person's orbital cavity, the prosthesis comprising:
(i) a solid rigid prosthetic eye body comprising an anterior convex surface through which an iris-cornea-sclera simulation is visible and a posterior surface, proximately conforming to a surface of the person's orbital cavity,
(ii) at least one chamber in the body defining a reservoir volume,
(iii) an access passage from the at least one chamber through the posterior surface of the body,
(iv) a cap releasably closing the access passage, and
(v) a bore opening from the at least one chamber through an orifice in the anterior surface of the body, there being a peripheral edge of the anterior surface around the orifice, the method comprising:
(I) providing an applicator device comprising:
 (A) a container comprising an open topped cavity containing a fluid that can be injected into the chamber of the prosthesis, and
 (B) a hollow tubular nozzle comprising:
  (i) a lengthwise tubular bore operatively connectable at an inside end to the open topped cavity of the container and having an outside end opening,
  (ii) a pointed outside end tip surface surrounding the outside end opening, and
  (iii) seating means that when the end tip surface is engaged against the orifice the end tip surface seats and seals said surface in the orifice in the anterior surface of the eye body,
 (D) connection means to connect the nozzle in the open top of the cavity, and
 (E) closure means to releasably close the end opening of the nozzle,
(II) releasing the closure means,
(III) locating the orifice by touching and moving the end tip surface of the nozzle on the anterior surface of the prosthesis,
(IV) seating the end tip surface in the orifice, pressuring the end tip surface of the nozzle to the orifice, and, while maintaining that pressure,
(V) ejecting fluid from the cavity of the container through the tubular bore of the nozzle into the bore opening through the anterior surface of the prosthesis and into the chamber.

17. The method of claim 16 wherein the self lubricating ocular prosthesis is in the person's orbital cavity and the locating the orifice comprises touching and moving the end tip surface of the nozzle on the anterior surface of the prosthesis.

18. The method of claim 16 wherein the self lubricating ocular prosthesis further comprises a depression in the anterior convex surface around the orifice and the locating the orifice comprises touching and moving the end tip surface of the nozzle on the depression on the anterior surface of the prosthesis.

19. The method of claim 16 wherein the seating means prevents the nozzle from significantly entering into the orifice bore opening through the anterior surface of the prosthesis when seating the end tip surface of the nozzle.

20. The method of claim 16 wherein the seating means comprises a diameter of the end tip surface larger than the bore opening and smaller than a depression in the anterior surface of the eye body around the orifice.

21. The method of claim 16 wherein the seating comprises engaging only the end tip surface against the peripheral edge of the anterior surface around the orifice.

22. The method of claim 16 wherein the end tip surface of the nozzle is composed of a polyolefin polymeric plastic.

23. The method of claim 16 wherein the container is compressible.

* * * * *